United States Patent [19]

Schanz Martin et al.

[11] Patent Number: 5,073,573
[45] Date of Patent: Dec. 17, 1991

[54] GEL COMPOSITIONS AND COSMETIC/COMPOSITIONS CONTAINING THE SAME

[75] Inventors: Roland Martin, Weinbeim; Klaus Schanz, Da-Schauernheim; Bruno Kaufmann, Frankenthal, all of Fed. Rep. of Germany

[73] Assignee: Giulini Chemie GmbH, Ludwigshafen, Fed. Rep. of Germany

[21] Appl. No.: 249,304

[22] Filed: Sep. 23, 1988

[30] Foreign Application Priority Data

Sep. 25, 1987 [DE] Fed. Rep. of Germany ....... 3732265

[51] Int. Cl.$^5$ .............. A61K 7/021; A61K 7/38; A61K 7/42; A61K 9/12
[52] U.S. Cl. ............... 514/844; 106/287.17; 424/DIG. 5; 424/47; 424/59; 424/60; 424/63; 424/64; 424/68; 514/846; 514/944
[58] Field of Search ................. 514/944, 844

[56] References Cited

U.S. PATENT DOCUMENTS

| | | | |
|---|---|---|---|
| 3,180,827 | 4/1965 | Martinek | 424/DIG. 5 |
| 4,071,374 | 1/1978 | Minton | 514/944 |
| 4,392,979 | 7/1983 | Lee et al. | 252/184 |
| 4,639,362 | 1/1982 | Schanz | 423/544 |
| 4,724,098 | 2/1988 | Kalz et al. | 423/544 |

FOREIGN PATENT DOCUMENTS 204240 12/1986 European Pat. Off. ........... 423/544
3408463 9/1985 Fed. Rep. of Germany ...... 423/544

Primary Examiner—Dale R. Ore
Attorney, Agent, or Firm—Spencer & Frank

[57] ABSTRACT

A gel composition useful as a thickening agent, for example in cosmetic compositions, containing an aluminum-magnesium-hydroxy compound of the general formula $$Al_xMg_y(OH)_{35-z}R_z \cdot nH_2O$$

where R represents the anion of a monocarboxylic acid having 2 to 22 carbon atoms and n, x, y and z are defined by $$0 \leq n \leq 10$$

$$3 \leq x \leq 9$$

$$4 \leq y \leq 13$$

$$3 \leq z \leq 5$$

and

$$3x + 2y = 35;$$

and also containing an organic, lipophilic compound which is liquid at 20° C.

20 Claims, 5 Drawing Sheets

GEL COMPOSITIONS AND COSMETIC/COMPOSITIONS CONTAINING THE SAME

CROSS-REFERENCE TO RELATED APPLICATION

This application is related to our concurrently filed application entitled "Aluminum Magnesium Hydroxy Compounds", application Ser. No. 07/248,950, the disclosure of which is incorporated herein by reference.

FIELD OF THE INVENTION

The present invention relates to a gel composition, useful for making cosmetics, composed of an aluminum-magnesium compound having a laminar structure and an organic lipophilic compound which is liquid at room temperature.

TECHNOLOGY BACKGROUND

Stability, ease of application, and reproducibility in manufacture of cosmetic preparations depend primarily on the rheological (fluid) properties of their components. Most cosmetic preparations contain gels which have a controlling influence on the rheological characteristics of the finished products. An important characteristic of cosmetic gels is their thixotropy. If thixotropic gels are subjected to increased shear forces, the viscosity of such gels is noticeably reduced. For example, when a shear force is applied, an apparently solid thixotropic substance becomes liquid for a period of time, but the original, solid gel structure slowly develops again once the shear force treatment ceases. This effect has wide utility in cosmetic and other preparations, such as in antiperspirants, creams, and nail enamels, but also in paints, inks and soaps.

Cosmetic gels are generally composed of a swellable argillaceous mineral which, upon taking up liquid, swells and forms a highly viscous gel. If the laminar structure of the argillaceous mineral is to be swelled by organic liquids, such as oils, fats and waxes, the argillaceous mineral must be modified to be organophilic or lipophilic.

Prior gel compositions contain argillaceous minerals having a layer structure, such as bentonite or montmorillonite, with a composition corresponding to the following formula:

$$(X, Y)_{2-3}(Si,Al)_4O_{10}(OH)_2Z_{\frac{1}{3}} \cdot n\ H_2O$$

where $X=Al$, $Fe(III)$, $Mn(III)$ or $Cr(III)$; $Y=Mg$, $Fe(II)$, $Mn(II)$, $Ni$, $Zn$ or $Li$ and $Z=K$, $Na$ or $Ca$.

Such a silicate is hydrophilic and is able to swell while absorbing a large quantity of water between its lattice planes to form aqueous gels having a high viscosity.

It is also known that an organophilic or lipophilic material can be produced from such a hydrophilic substance by ion exchange. For example, $Na^+$ ions in the original material can be replaced by quaternary ammonium cations having long-chain organic groups (see J. W. Jordan, Jour. Phys. and Colloid Chem. 53, p. 294 (1949), and J. W. Jordan et al, Kolloid Z, 137 p. 40, (1954) or U.S. Pat. Nos. 4,724,098 and 4,434,076). Materials produced in this manner are called "organically modified." These organically modified argillaceous minerals exhibit a good swelling effect in oils, fats and waxes and form viscous gels with them if mechanical energy is applied, suitable additives are added and the temperature is suitable.

A gel composition is also known which includes an organically modified or unmodified argillaceous mineral of the montmorillonite series, a surfactant and an organic solvent (F. Gstirner, Grundstoffe und Verfahren der Arzneimittelzubereitung [Basic Ingredients and Methods of Pharmaceutical Preparation] page 715, 1960). However, the gel forming ability of these montmorillonites is very low so that large quantities of expensive montmorillonite must be used. However, when pigments are added to these compositions, the pigments separate easily and the desired viscosity of the gel preparation is not readily maintained.

Other gel compositions include 10% organically modified montmorillonite, 86.7% mineral oil and 3.3% wetting agent (also called a polar additive; H. P. Fiedler, Lexikon der Hilfsstoffe [Encyclopedia of Auxiliary Substances], EDITIO Cantor Aulendorf [Cantor Aulendorf Edition], page 167).

A particular drawback of prior gel preparations is that the high percentages of organic polar additives employed, such as methanol, ethanol, and acetone, and the quaternary ammonium salts introduced by ion exchange, have a skin-irritating effect and may even cause allergic reactions. Moreover, the impurities of the montmorillonite minerals and the various organic additives produce a yellow to brown coloration and an unpleasant odor. These are especially disadvantageous when the preparations are to be used in cosmetics.

SUMMARY OF THE INVENTION

It is therefore an object of the present invention to discover novel gel compositions which include swellable, gel-forming compounds having a laminar structure and which do not have the above-mentioned drawbacks of the prior compositions. It is another object of the invention to drastically reduce the quantity of polar additives contained in the compositions. Another object is to discover suitable organic compounds which are liquid t room temperature and which ensure swelling of the gel-forming compound.

This is accomplished by a gel composition useful as a thickening agent, containing an aluminum-magnesium-hydroxy compound having a laminar structure, of the general formula $$Al_xMg_y(OH)_{35-z}R_z \cdot n\ H_2O$$

where R represents the anion of a monocarboxylic acid having 2 to 22 carbon atoms and x, y and z meet the following conditions:

$3 \leq x \leq 9$ $4 \leq y \leq 13$ $3 \leq z \leq 5$ and $0 \leq n \leq 10$ m is a number in the range 0 to 10

$3x + 2y = 35;$ and also containing an organic, lipophilic compound which is liquid at 20° C. With this gel composition, the above-mentioned drawbacks can be overcome.

DETAILED DESCRIPTION OF THE INVENTION

The aluminum-magnesium-hydroxy compounds of the invention have a laminar structure and exhibit very good gel formation in organic liquids.

Compounds in which $x=5$, $y=10$ and $z=4$ are particularly suitable. Advantageously, industrial grade mixtures of aliphatic monocarboxylic acids having 16 to 18 carbon atoms are used in the synthesis of the compounds.

The compounds are produced by reacting, under stirring and at temperatures between about 20° C. and 100° C. (preferably between about 20° C. and 60° C.) an aqueous suspension of a compound of the formula $Al_x Mg_y(OH)_{35-z}(SO_4)_{z/2} \cdot nH_2O$ in which x, y and z have the above-stated meaning, with, for example, an aqueous suspension of an alkali salt of a monocarboxylic acid which contains 2 to 22 carbon atoms. Preferably the reaction is performed with shear forces acting on the reaction mixture. Under such process conditions, the reaction is completed after 2 hours in many cases.

The separation of the reaction product from the aqueous suspension can be effected according to a known process, but preferably by filtration. The filter cake should be washed with water, to remove the adhering alkali sulfate until no further $SO_4^{2-}$ can be found by barium chloride in the wash water. The filter cake is dried at temperatures between about 60° C. and 130° C., preferably, however at about 80° C. to 110° C., for example in a shelf dryer. Other types of drying devices can also be used.

In another drying variation, the filter cake, once it is free of sulfate, is resuspended in water and is spray-dried, with the entrance temperature $T_E$=about 250° C. to 350° C., preferably about 270° C. to 300° C., and the exit temperature $T_A$=about 80° C. to 130° C., preferably 90° C. to 110° C.

According to other variations of the process, the alkali salt of a monocarboxylic acid is added in solid form to the aqueous suspension of the compound $Al_x Mg_y(OH)_{35-z}(SO_4)_{z/2} \cdot nH_2O$, with all other process features remaining the same.

The Al-Mg compounds employed as starting materials in the process are known in the art. For example, they are disclosed in U.S. Pat. No. 4,639,362. Monocarboxylic acids are commercially available compounds. Industrial grade mixtures of monocarboxylic acids may be used. The alkali salts can be produced as indicated in the examples.

Figure 1:
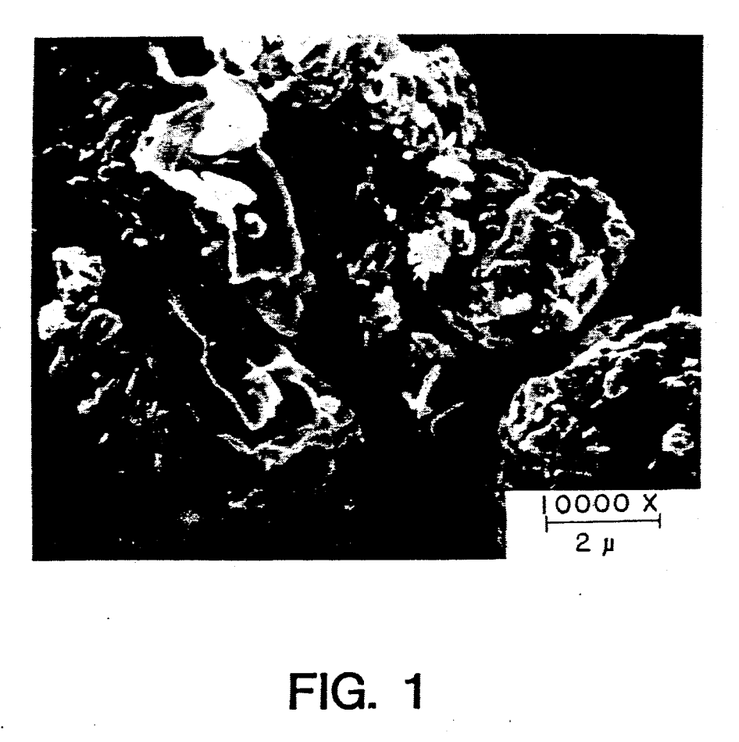
FIG. 1 is a microphotograph showing the laminar structure of the product from Example 10.

The novel compounds are solid, white and odorless, crystalline substances. Their structure is characterized with the aid of X-ray diffraction and scanning electron microscopy. X-ray diffraction patterns show that the novel compounds are crystalline. The layer or laminar structure is evident from scanning electron micrographs (see FIG. 1).

In comparison with commercially available organically modified hectorite or sodium bentonite, the compounds of the invention are noticeably whiter. The degree of whiteness is a measure of the color of the substances and was determined by means of a Tricolor LFM 3 color measuring device (manufactured by Dr. Lange) against an enamel white standard. Table 1 shows the whiteness of the products from Examples 6 to 17 below and the whiteness of two commercially available products. This table clearly shows that the compounds of the invention have a noticeably higher degree of whiteness than the commercially available products.

TABLE 1

| Comparison of Whiteness | |
| --- | --- |
| Product of Example 6: | 98.1 |
| Product of Example 7: | 98.0 |
| Product of Example 8: | 98.1 |
| Product of Example 9: | 98.2 |
| Product of Example 10: | 97.9 |
| Product of Example 11: | 98.4 |
| Product of Example 12: | 98.3 |
| Product of Example 13: | 98.2 |
| Product of Example 14: | 98.1 |
| Product of Example 15: | 98.3 |
| Product of Example 16: | 98.4 |
| Product of Example 17: | 98.1 |
| Sodium bentonite | 91.3 |
| Organically modified hectorite | 91.8 |

The experiments described below show the efficiency of the novel product as an anti-settling agent in a concentration of 2% by weight.

Formulations were produced as described in Table 2 and the "settling curve" was determined by way of turbidity measurements made with the aid of an Eppendorf photometer.

In a 300 ml beaker, the optical extinction of the paraffin oil solvent was set at 0 (100% transmissibility). The same beaker was used for each test. All samples were tested at a 2% by weight concentration in paraffin oil. They were homogeneously suspended by stirring and were then stirred for 3 minutes at 100 rpm. The stirrer was turned off and the decrease of extinction monitored on a graph. The transmissibility value obtained immediately after stopping the stirrer was set to 0%.

Table 2 clearly shows that the products produced according to the present invention settle much less easily than the comparison products. This is an advantage when using the products, for instance, in connection with pigments and less soluble dyes.

TABLE 2

| | Settling Tests (% Transmissibility) | | | | |
| --- | --- | --- | --- | --- | --- |
| Product of Example | 1 h | 2 h | 3 h | 6 h | 8 h |
| 6 | 0.2 | 0.4 | 1.0 | 11.9 | 21.0 |
| 7 | 0.8 | 1.2 | 1.4 | 4.7 | 9.0 |
| 8 | 1.0 | 2.0 | 2.8 | 13.6 | 23.5 |
| 9 | 0.8 | 0.8 | 1.2 | 4.7 | 8.5 |
| 10 | 0.8 | 0.8 | 0.8 | 3.5 | 7.0 |
| 11 | 0.8 | 0.8 | 1.2 | 2.5 | 5.8 |
| 12 | 0.4 | 0.4 | 0.4 | 1.6 | 5.5 |
| 13 | 0.2 | 0.2 | 0.2 | 1.5 | 5.3 |
| 14 | 0.2 | 0.2 | 0.3 | 1.5 | 5.0 |
| 15 | 0.2 | 0.2 | 0.2 | 1.6 | 5.4 |
| 16 | 0.4 | 0.6 | 0.8 | 2.0 | 6.1 |
| 17 | 0.6 | 0.6 | 1.0 | 2.5 | 6.3 |
| Na-bentonite | 2.3 | 7.6 | 12.5 | 33.0 | 51.0 |
| organically modified | 2.0 | 6.5 | 9.0 | 22.2 | 33.0 |

TABLE 2-continued

| | Settling Tests (% Transmissibility) | | | | |
|---|---|---|---|---|---|
| Product of Example | 1 h | 2 h | 3 h | 6 h | 8 h |
| hectorite | | | | | 5 |

Separately from the above determination, the "settling volume" was determined as a function of time in a 100 ml measuring cylinder. For this purpose, the preparation was shaken 20 times vertically and 20 times horizontally and was then allowed to settle. The settling volume provides information about the easy dispersibility of the organic products of the present invention in a particular solvent under the influence of low shear forces.

In contrast to the settling tests reflected in Table 2, the products in Tables 3 and 4 were suspended (in a 2% by weight concentration) in the respective solvent together with a substance which is not soluble in this solvent (e.g. aluminum chlorhydrate having a grain size of 90% in a range between 10 $\mu$m and 75 $\mu$m) in a 15% concentration. It can be seen that the suspended products settle less easily if the substances from Examples 6 to 11 are added.

TABLE 3

| | Settling volume (ml) in Silicone Oil (Type 345 - Dow Corning) | | | | | | | | | |
|---|---|---|---|---|---|---|---|---|---|---|
| Product from | 0.5 min | 1 min | 3 min | 7 min | 10 min | 20 min | 30 min | 60 min | 2 h | 14 h |
| Example 6 | 99 | 98 | 98 | 91 | 90 | 80 | 75 | 65 | 53 | 23 |
| Example 7 | 100 | 100 | 99 | 98 | 97 | 93 | 89 | 74 | 58 | 24 |
| Example 8 | 100 | 100 | 98 | 96 | 95 | 90 | 85 | 72 | 56 | 24 |
| Example 9 | 100 | 99 | 98 | 96 | 94 | 88 | 82 | 77 | 61 | 27 |
| Example 10 | 100 | 99 | 98 | 96 | 94 | 89 | 81 | 70 | 54 | 27 |
| Example 11 | 100 | 99 | 97 | 94 | 92 | 84 | 78 | 67 | 54 | 25 |
| without additive | 98 | 95 | 73 | 44 | 40 | 35 | 32 | 30 | 25 | 25 |
| Na-bentonite | 100 | 99 | 97 | 82 | 68 | 47 | 43 | 38 | 35 | 25 |
| org. modified hectorite | 100 | 99 | 97 | 92 | 91 | 82 | 72 | 62 | 50 | 27 |

TABLE 4

| | Settling Volume (ml) in Paraffin Oil (Type Pioneer 2660, highly viscous) - Hansen + Rosenthal | | | | | | | | |
|---|---|---|---|---|---|---|---|---|---|
| Product from | 10 min | 30 min | 1 h | 2 h | 3 h | 4 h | 8 h | 18 h | 24 h |
| Example 6 | 100 | 98 | 97 | 91 | 87 | 82 | 59 | 45 | 43 |
| Example 7 | 100 | 99 | 98 | 96 | 94 | 93 | 77 | 47 | 43 |
| Example 8 | 100 | 99 | 98 | 94 | 92 | 89 | 71 | 48 | 43 |
| Example 9 | 100 | 99 | 97 | 94 | 91 | 89 | 72 | 44 | 43 |
| Example 10 | 100 | 99 | 98 | 94 | 92 | 90 | 73 | 45 | 43 |
| Example 11 | 100 | 98 | 98 | 93 | 91 | 88 | 67 | 45 | 43 |
| Na-bentonite | 100 | 96 | 87 | 61 | 53 | 49 | 44 | 43 | 43 |
| org. modified hectorite | 99 | 98 | 97 | 91 | 85 | 80 | 58 | 45 | 43 |
| without additive | 97 | 94 | 84 | 60 | 50 | 47 | 41 | 40 | 40 |

The invention will now be described in greater detail by way of the following examples which are intended only to illustrate specific embodiments of the invention, and not to limit it. Unless otherwise stated, all parts and percentages are by weight.

EXAMPLE 1

Production of $Al_xMg_y(OH)_{35-z}(SO_4)_{z/2} \cdot nH_2O$

In an open basin 743 g aluminum hydroxide paste containing 72.73% $Al_2O_3$ was diluted with 8995 g water and then 2924.8 g aluminum sulfate solution containing 21.54% $SO_4$ and 4.21% Al were stirred in. The suspension was allowed to stand overnight to permit any $CO_2$ to escape. Then, 1336.7 g MgO containing 60.3% Mg were added under stirring, causing slight heating. Stirring continued for 2 hours and then the suspension was ready for further processing.

Analysis: 2.46% Al; 4.47% Mg, 3.5% $SO_4$

EXAMPLE 2

Production of sodium caprylate - $C_7H_{15}COO$ Na 800 g caprylic acid was suspended in 7 L water and heated under stirring to 80° C. Then, a solution of 221.8 g NaOH in 500 g water was slowly added and the mixture was cooled to room temperature. The aqueous solution was slowly evaporated and the residue was dried at 105° C. in a drying cabinet. Yield: 877 g (95% theoretical) of a white powder.

EXAMPLE 3

Production of sodium myristate - $C_{13}H_{27}COO$ Na.

800 g myristic acid was suspended in 3 L water and the suspension was heated under stirring to 80.C. Then, a solution of 140.2 g NaOH in 350 ml water wa slowly added and the mixture permitted to cool to room temperature. This precipitated the sodium myristate and it was filtered using a suction filter. The product was dried carefully in a drying cabinet until a constant weight was obtained.

Yield: 820 g (89% theoretical) of a white powder.

EXAMPLE 4

Production of sodium palmitate - $C_{15}H_{31}COO$ Na 800 g palmitic acid was suspended in 9 L water and heated under stirring to 80° C. Then a solution of 124.8 g NaOH in 350 ml water was added and the mixture was permitted to cool to room temperature. The residue was filtered out and dried at 105° C. in a drying cabinet.

Yield: 814 g (94% theoretical) of a white powder.

EXAMPLE 5

Production of sodium behenate - $C_{21}H_{43}COO$ Na 700 g behenic acid was suspended in 9000 ml water and heated to 80° C. Then a solution of 83 g NaOH in 350 ml distilled water was added. This immediately precipitated the sodium behenate. The suspension was permitted to cool to room temperature and the precipitate was filtered using a suction filter. It was rinsed three times in 200 ml each and the residue dried at 65° C. in a drying cabinet.

Yield: 708 g (95% theoretical) of a white powder.

EXAMPLE 6

Production of $Al_5Mg_{10}(OH)_{31}(CH_3COO)_4$ 119.6 g sodium acetate was suspended with stirring in 1076 g water and was then added to 2000 g of an Al-Mg-hydroxy sulfate suspension produced as in Example 1. The mixture was heated to 80° C. for three hours to complete the reaction, then the suspension was permitted to cool and the insoluble Al-Mg-hydroxy acetate was filtered out. The filtrate was rinsed in water until no further sulfate could be detected. The filter cake was then dried at 105° C. in a drying cabinet until a constant weight was attained.

Yield: 395 g (95% theoretical). Description: white, odorless, crystalline powder. Analysis: 11.5% Al in dry state (theory: 11.8%); 20.9% Mg in dry state (theory: 21.3%); 8.3% C in dry state (theory: 8.4%).

X-ray Powder Pattern (Apparatus: Philipps Automated X-Ray Powder Diffractometer, System APD 15) for Example 6

| Peak No. | 2-theta | d (pm) | $I/I_o$ |
|---|---|---|---|
| 1 | 19.870 | 4 46.45 | 82 |
| 2 | 34.170 | 2 62.18 | 56 |
|   | 34.484 | 2 59.86 | 74 |
|   | 35.669 | 2 55.07 | 100 |
|   | 35.669 | 2 51.50 | 77 |
| 3 | 41.400 | 2 17.00 |  |
| 4 | 42.500 | 2 13.00 |  |
| 5 | 48.200 | 1 89.00 |  |
| 6 | 60.309 | 1 53.34 | 49 |
|   | 60.526 | 1 52.84 | 66 |
|   | 61.199 | 1 51.32 | 76 |
|   | 61.633 | 1 50.35 | 60 |
|   | 61.965 | 1 49.63 | 58 |

EXAMPLE 7

Production of Al-Mg-hydroxy caprylate $Al_5Mg_{10}(OH)_{31}(C_7H_{15}COO)_4$ 242.3 g sodium caprylate (from Example 2) was suspended in 2181 g water with stirring and was added to 2000 g Al-Mg-hydroxy sulfate suspension produced as in Example 1. The suspension was heated to 60° C. for one hour to complete the reaction, was permitted to cool and then the insoluble Al-Mg-hydroxy caprylate was filtered off. The filtrate was rinsed with water until no further sulfate could be detected. The filter cake was then dried at 105° C. in a drying cabinet until a constant weight was attained.

Yield: 517 g (96% theoretical). Description: white, odorless, crystalline powder Analysis: 9.0% Al in dry state (theory: 9.1%); 16.2% Mg in dry state (theory: 16.4%); 25.0% C in dry state (theory: 26.0%).

X-ray Powder Pattern (Apparatus: Philipps Automated X-Ray Powder Diffractometer, System APD 15) for Example 7

| Peak No. | 2-theta | d (pm) | $I/I_o$ |
|---|---|---|---|
| 1 | 19.370 | 4 57.84 | 66 |
| 2 | 33.974 | 2 63.65 | 42 |
|   | 34.267 | 2 61.46 | 72 |
|   | 34.506 | 2 59.70 | 88 |
|   | 34.871 | 2 57.07 | 100 |
|   | 35.075 | 2 55.62 | 83 |
|   | 35.608 | 2 51.91 | 62 |
| 3 | 41.4 | 2 17. |  |
| 4 | 42.5 | 2 13. |  |
| 5 | 48.3 | 1 89. |  |
| 6 | 60.652 | 1 525.5 | 67 |
|   | 60.892 | 1 520.1 | 72 |
|   | 61.279 | 1 511.4 | 56 |
|   | 61.714 | 1 501.8 | 46 |

EXAMPLE 8

Production of Al-Mg-hydroxy myristate $Al_5Mg_{10}(OH)_{31}(C_{13}H_{27}COO)_4$ 182.5 g sodium myristate (from Example 3) was suspended in water by stirring and was added to 1000 g of a Al-Mg-hydroxy sulfate suspension produced as in Example 1. The suspension was heated to 60° C. for one hour to complete the reaction, was permitted to cool and the insoluble Al-Mg-hydroxy myristate was then filtered off. The filtrate was rinsed with water until no further sulfate could be detected. The filter cake was then dried at 105° C. in a drying cabinet until a constant weight was attained.

Yield: 321 g (97% theoretical). Description: white, odorless, crystalline powder Analysis: 7.3% Al in dry place state (theory: 7.4%); 13.2% Mg in dry place state (theory: 13.4%); 36.3% C in dry state (theory: 37.0%).

X-ray Powder Pattern (Apparatus: Philipps Automated X-Ray Powder Diffractometer, System APD 15) for Example 8

| Peak No. | 2-theta | d (pm) | $I/I_o$ |
|---|---|---|---|
| 1 | 20.909 | 4 24.48 | 100 |
|   | 21.340 | 4 16.00 | 91 |
|   | 21.560 | 4 11.82 | 72 |
| 2 | 33.916 | 2 64.08 | 35 |
|   | 34.089 | 2 62.78 | 49 |
|   | 34.471 | 2 59.95 | 70 |
|   | 35.069 | 2 55.66 | 68 |
|   | 35.524 | 2 52.49 | 51 |
| 3 | 41.4 | 217. |  |
| 4 | 42.5 | 213. |  |
| 5 | 48.2 | 189. |  |
| 6 | 60.318 | 1 53.31 | 28 |
|   | 60.534 | 1 52.82 | 47 |
|   | 61.649 | 1 50.32 | 42 |

EXAMPLE 9

Production of Al-Mg-hydroxy palmitate $Al_5Mg_{10}(OH)_{31}(C_{15}H_{31}COO)_4$ 405.9 g sodium palmitate (from Example 4) was suspended by stirring in 3653 g water and was added to 2000 g Al-Mg-hydroxy sulfate suspension produced as in Example 1. The suspension was heated to 60° C. for one hour to complete the reaction, was permitted to cool and then the insoluble Al-Mg-hydroxy palmitate was filtered off. The filtrate was rinsed with water until no further sulfate could be detected. The filter cake was then dried at 105° C. in a drying cabinet until a constant weight was attained.

Yield: 660 g (94% theoretical). Description: white, odorless, crystalline powder Analysis: 6.8% Al in dry state (theory: 7.0%); 12.4% Mg in dry state (theory: 12.6%); 39.4% C in dry state (theory: 39.9%).

X-ray Powder Pattern (Apparatus: Philipps Automated X-Ray Powder Diffractometer, System APD 15) for Example 9

| Peak No. | 2-theta | d (pm) | $I/I_o$ |
|---|---|---|---|
| 1 | 19.702 | 4 50.21 | 59 |
|   | 21.323 | 4 16.35 | 100 |
| 2 | 31.792 | 2 81.23 | 30 |
| 3 | 34.305 | 2 61.17 | 48 |
|   | 34.615 | 2 58.91 | 76 |
|   | 35.169 | 2 54.95 | 64 |
| 4 | 41.4 | 2 17. |  |

-continued

X-ray Powder Pattern (Apparatus: Philipps Automated X-Ray Powder Diffractometer, System APD 15) for Example 9

| Peak No. | 2-theta | d (pm) | I/I$_o$ |
|---|---|---|---|
| 5 | 42.5 | 2 13. | |
| 6 | 48.3 | 1 89. | |
| 7 | 60.700 | 1 52.44 | 49 |
| | 61.138 | 1 51.45 | 32 |

EXAMPLE 10

Production of Al-Mg-hydroxy stearate
Al$_5$Mg$_{10}$(OH)$_{31}$(C$_{17}$H$_{35}$COO)$_4$ 446.8 g sodium stearate was suspended by stirring in 4021 g water and was added to 2000 g Al-Mg-hydroxy sulfate suspension produced as in Example 1. The suspension was heated to 60° C. for one hour to complete the reaction, was permitted to cool and then the insoluble Al-Mg-hydroxy stearate was filtered off. The filtrate was rinsed until no further sulfate could be detected. The filter cake was then dried in a drying cabinet at 105° C. in a drying cabinet until a constant weight was attained.

Yield: 738 g (98% theoretical). Description: white, odorless, crystalline powder. Analysis: 6.5% Al in dry state (theory: 6.6%); 11.7% Mg in dry state (theory: 11.9%); 42.2% C in dry state (theory: 42.4%)

Peak pattern for Example 10:

X-ray Powder Pattern (Apparatus: Philipps Automated X-Ray Powder Diffractometer, System APD 15) for Example 10

| Peak No. | 2-theta | d (pm) | I/I$_o$ |
|---|---|---|---|
| 1 | 19.576 | 4 53.07 | 59 |
| | 20.794 | 4 26.81 | 91 |
| | 21.466 | 4 13.59 | 100 |
| 2 | 31.641 | 2 82.53 | 34 |
| 3 | 34.894 | 2 64.25 | 41 |
| | 34.072 | 2 62.91 | 36 |
| | 34.401 | 2 60.47 | 47 |
| | 34.697 | 2 58.32 | 61 |
| | 35.265 | 2 54.29 | 46 |
| | 35.5114 | 2 52.56 | 44 |
| | 35.693 | 2 51.33 | 39 |
| | 35.873 | 2 50.11 | 34 |
| 4 | 41.4 | 2 17. | |
| 5 | 42.5 | 2 13. | |
| 6 | 48.163 | 1 88.77 | 30 |
| 7 | 60.399 | 1 53.13 | 26 |
| | 60.765 | 1 52.29 | 37 |
| | 60.974 | 1 51.82 | 35 |
| | 61.306 | 1 51.08 | 35 |

Thermoanalyses for Example 10 in Example 1. The suspension was heated to 60° C. for one hour to complete the reaction, was permitted to cool and then the insoluble Al-Mg-hydroxy behenate was filtered off. The filtrate was rinsed with water until no further sulfate could be detected. The filter cake was then dried at 105° C. in a drying cabinet until a constant weight was attained.

Yield: 767 g (95% theoretical). Description: white, odorless, crystalline powder. Analysis: 5.8% Al in dry state (theory: 6.0%); 10.5% Mg in dry state (theory: 10.7%); 46.2% C in dry state (theory: 46.7%).

| Peak No. | 2-theta | d (pm) | $I/I_o$ |
|---|---|---|---|
| 1 | 19.584 | 4 52.90 | 67 |
|   | 21.049 | 4 21.69 | 82 |
|   | 21.260 | 4 17.56 | 100 |
| 2 | 31.851 | 2 80.72 | 43 |
| 3 | 34.074 | 2 62.89 | 46 |
|   | 34.630 | 2 58.80 | 61 |
|   | 34.857 | 2 57.17 | 73 |
|   | 35.176 | 2 54.90 | 54 |
|   | 35.686 | 2 51.38 | 52 |
| 4 | 41.4 | 2 17. |   |
| 5 | 42.5 | 2 13. |   |
| 6 | 48.3 | 1 89. |   |
| 7 | 60.705 | 1 52.43 | 43 |
|   | 61.982 | 1 49.59 | 28 |

EXAMPLE 12

Production of Al-Mg-hydroxy stearate
$Al_3Mg_{13}(OH)_{31}(C_{17}H_{35}COO)_4$

In an open basin, 578.2 g aluminum hydroxide paste containing 12.73% $Al_2O_3$ was diluted with 3151.4 g water and then 796 g aluminum sulfate solution containing 4.22% Al and 21.62% $SO_4$ was stirred in. The suspension was allowed to stand overnight to permit any $CO_2$ gas to escape and then 474 g MgO (commercially available) containing 99% MgO was added under stirring. This caused slight heating.

Analysis of the suspension: 1.40% Al, 5.60% Mg, 3.46% $SO_4$.

Under stirring, 969 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1606 g (97% theoretical). Description: white, odorless, crystalline powder. Analysis: 3.7% Al in dry state (theory: 3.9%); 15.3% Mg in dry state (theory: 15.4%); 40.8% C in dry state (theory: 41.5%).

EXAMPLE 13

Production of Al-Mg-hydroxy stearate
$Al_5Mg_{10}(OH)_{31}(C_{17}H_{35}COO)_4$

In an open basin, 1581 g aluminum hydroxide paste containing 12.3% $Al_2O_3$ was diluted with 3000 g water and then 975 g aluminum sulfate solution containing 4.21% Al and 21.54% $SO_4$ was stirred in. The suspension was allowed to stand overnight to permit any $CO_2$ to escape and then 446 MgO (99% purity) was added under stirring. This caused slight heating.

EXAMPLE 11

Production of Al-Mg-hydroxy behenate
$Al_5Mg_{10}(OH)_{31}(C_{21}H_{43}COO)_4$ 528.6 g sodium behenate (from Example 5) was suspended by stirring in 4758 g water and was added to 2000 g Al-Mg-hydroxy sulfate suspension produced as Analysis of the suspension: 2.41% Al, 4.40% Mg, 3.45% SO$_4$.

While stirring, 983 g sodium stearate suspended in 7000 g water were added to 4470 g of the above suspension. The suspension was heated to 60° C. for one hour, was permitted to cool and then the insoluble Al-Mg-hydroxy stearate wa filtered off. The filtrate was rinsed with water until no further sulfate could be detected. The filter cake was again suspended in 10 kg water and was spray-dried. The entrance temperature used was 275° C. and the exit temperature was 100° C.

Yield: 1556 g (95% theoretical). Description: white, odorless, crystalline powder. Analysis: 6.5% Al in dry state (theory: 6.6%); 11.7% Mg in dry state (theory: 11.9%); 42.0% C in dry state (theory: 42.4%). Density: 1.19 g/ml

EXAMPLE 14

Production of Al-Mg-hydroxy stearate
Al$_7$Mg$_7$(OH)$_{31}$(C$_{17}$H$_{35}$COO)$_4$ In an open basin, 2086 g aluminum hydroxide paste containing 12.73% Al$_2$O$_3$ was diluted with 1825 g water and then 824 g aluminum sulfate solution containing 4.22% Al and 21.62% SO$_4$ was stirred in. The suspension was allowed to stand overnight to permit any CO$_2$ to escape and then 264 MgO containing 99% MgO was added with stirring. This caused slight heating.

Analysis of the suspension: 3.4% Al, 3.2% Mg, 3.7% SO$_4$.

With stirring, 1054 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1668 g (96% theoretical). Description: white, odorless, crystalline powder. Analysis: 9.2% Al in dry state (theory: 9.3%); 8.1% Mg in dry state (theory: 8.4%); 41.9% C in dry state (theory: 42.3%).

EXAMPLE 15

Production of Al-Mg-hydroxy stearate
Al$_9$Mg$_4$(OH)$_{31}$(C$_{17}$H$_{35}$COO)$_4$ In an open basin, 2881 g aluminum hydroxide paste containing 12.73% Al$_2$O$_3$ was diluted with 1126 g water and then 839 g aluminum sulfate solution containing and 4.22% Al and 21.62% SO$_4$ was stirred in. The suspension was allowed to stand overnight to permit any CO$_2$ to escape and then 154 MgO (99% purity) was added with stirring. This caused slight heating.

Analysis of the suspension: 4.32% Al, 4.87% Mg, 3.85% SO$_4$.

Under stirring 1,098 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1685 g (94% theoretical). Description: white, odorless, crystalline powder. Analysis: 12.0% Al in dry state (theory: 12.1%); 4.7% Mg in dry state (theory: 4.9%); 42.4% C in dry state (theory: 42.7%).

EXAMPLE 16

Production of Al-Mg-hydroxy stearate
Al$_5$Mg$_{10}$(OH)$_{31}$(C$_{17}$H$_{35}$COO)$_4$ In a stirring basin, I1.1 kg aluminum hydroxide paste containing 12.73% Al$_2$O$_3$ was diluted with 30 kg water and then 6.8 kg aluminum sulfate solution containing 4.2% Al and 21.5% SO$_4$ was stirred in. Stirring continued for three hours and then 3.1 kg MgO containing 99% MgO were added. This caused slight heating. After 3 further hours of stirring, 7.2 kg sodium stearate and 49 kg water were added. Stirring continued and for another two hours and then the suspension was treated with high shear forces to obtain a homogeneous paste. After further stirring (about one hour), the insoluble Al-Mg-hydroxy stearate was filtered using a filter press. The filtrate was rinsed with water until no sulfate could be detected. The filter cake was suspended in 70 kg water and spray-dried. The entrance temperature was 280° C. and the exit temperature was 90° C.

Yield: 10.5 kg (92% theoretical). Description: white, odorless, crystalline powder. Analysis: 6.5% Al in dry state (theory: 6.6%); 11.8% Mg in dry state (theory: 11.9%); 42.1% C in dry state (theory: 42.4%).

EXAMPLE 17

Production of Al-Mg-hydroxy palmitate stearate
Al$_5$Mg$_{10}$(OH)$_{31}$(C$_{15}$H$_{31}$COO) (C$_{17}$H$_{35}$COO)$_3$ 101 g sodium palmitate (from Example 4) and 335 g sodium stearate were suspended by stirring in 3930 g water and were added to 2000 g Al-Mg-hydroxy sulfate suspension produced as in Example 1. The suspension was homogenized in a "Turrax" stirrer and was stirred for three hours at room temperature. Then the suspension was filtered and freed of sulfates by rinsing with distilled water. The filter cake was dried at 95° C. in a drying cabinet until a constant weight was attained.

Yield: 693 g (95% theoretical). Description: white, odorless, crystalline powder. Analysis: 6.6% Al in dry state (theory: 6.7%); 11.5% Mg in dry state (theory: 12.0%);
41.4% C in dry state (theory: 41.8%).

The concentration of the aluminum-magnesium-hydroxy compound in the gel composition should lie between 5 and 25 weight percent with reference to the gel composition, and preferably between 10 and 20 weight percent.

The organic compound which is liquid at room temperature and in which the gel formation takes place can be selected from the group including
a) vegetable and animal fats, oils and waxes (e.g. castor oil, jojoba oil, wool waxes);
b) paraffin hydrocarbons (having a boiling range between about 170° C. and 550° C.);
c) silicone oils (e.g. dimethicone, cyclomethicone tetramer and pentamer);
d) aliphatic and aromatic esters (e.g. isopropyl myristate, isopropyl palmitate, di-octyl adipate);
e) higher alcohols and ethers (e.g. polyethylene glycol, 2-octyl-dodecanol). The higher alcohols and ethers have at least 4 carbon atoms, preferable 6 to 30 carbon atoms in the molecule.

Mixtures of compounds of one group may also be combined if they are compatible with one another.

The concentration of the organic lipophilic compound should lie between about 95 and 75 weight percent, with reference to the gel composition, preferably between about 90 and 80%.

According to a particularly favorable embodiment, the gel compositions further include a polar additive in quantities up to about 20 weight %, with reference to the aluminum-magnesium-hydroxy compound. In many cases, quantities up to about 1 weight percent are sufficient. It should be noted that the additive may even be omitted.

Mixtures of water/methanol, water/ethanol, or water/acetone may be employed as polar additives.

The quantity of water in this mixtures should be 5 to 25% by weight, preferable 8 to 12%.

Acetone, propylene carbonate and polyoxyethylene-(4)-lauryl alcohol are also suitable as polar additives.

The gel composition is produced as follows: the powdered aluminum-magnesium-hydroxy compound, the optional polar additive and the lipophilic compound, which is liquid at room temperature, are heated to about 120° C. to 130° C. in a suitable mixer and with the use of high shear forces. The resulting gel has a "Vaseline"-like consistency and is transparent to white. It is an excellent rheological additive and anti-settling agent for cosmetics.

The examples below describe in greater detail the production and physical properties of the gels of the present invention, such as their viscosity, color, odor, stability, thixotropy and settling behavior.

The consistency of highly viscous gels is determined with the aid of the micropenetration method. Measurements are made with a penetrometer made by Sommer & Runge, Berlin, by means of a fall rod weighing 5 g which, after release, penetrates for 5 seconds into the gel to be measured. The penetration depth is indicated in steps of 0.1 mm.

Figure 2:
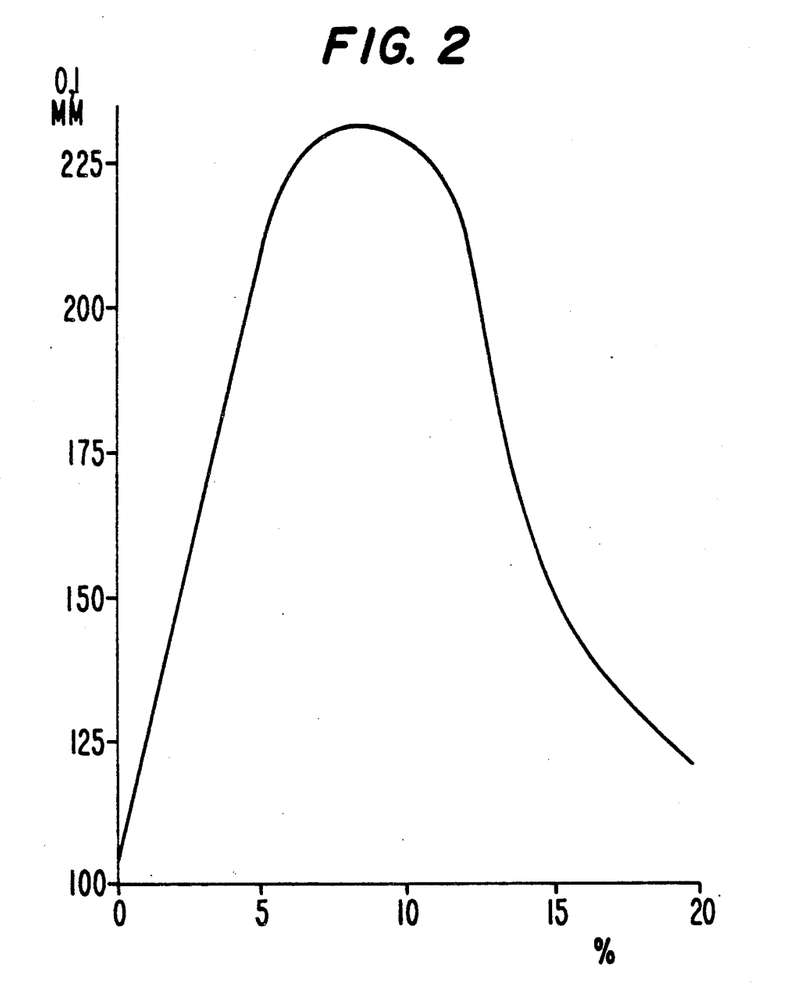
FIG. 2 is a graph showing the extent of micropenetration of gels from Examples 6-10 as a function of the quantity of polar additive used.

FIG. 2 shows the decrease in viscosity of the gel with an increasing quantity of polar additives, down to a minimum and a subsequent increase.

EXAMPLES 18 TO 24

Production of mineral oil gels including different polar additives.

In a 400 ml beaker, 20 g of the aluminum-magesium-hydroxy-stearate powder from Example 17 was suspended in paraffin oil (type "Pioneer 2660", highly viscous, made by Hansen & Rosenthal, Hamburg) and was heated under stirring to 90° C. with the aid of a heating plate. Then the polar additive was added and the mixture was heated under stirring to about 120° C. until the suspension began to foam slightly. The foaming results from traces of water. Without being cooled further, the suspension was treated for about 30 seconds with high shear forces (for example, using an IKA-Laboratory "Turrax" stirrer) until it thickened. Then the suspension was cooled under vacuum in a desiccator and with slight stirring.

The result in each case was a colorless, transparent gel of different viscosity.

TABLE 5

Production of Mineral Oil Gels Containing Different Polar Additives

| Example No. | Paraffin Oil (g) | Polar Additive Type | (g) | %* | Yield (g) | (%) |
|---|---|---|---|---|---|---|
| 18 | 180 | — | — | — | 200 | 100 |
| 19 | 180 | A | 0.1 | 0.5 | 199 | 99 |
| 20 | 179 | A | 1 | 5 | 199 | 99 |
| 21 | 178 | A | 2 | 10 | 197 | 98 |
| 22 | 176 | A | 4 | 20 | 195 | 97 |
| 23 | 179 | B | 1 | 5 | 199 | 99 |
| 24 | 178 | C | 1 | 5 | 198 | 99 |

*with reference to the powder employed
A = polyoxyethylene-(4)-lauryl alcohol
B = ethanol/H$_2$O 95/5
C = propylene carbonate

EXAMPLES 25 TO 28

Production of mineral oil gels including Al-Mg-hydroxy stearates of different compositions In a 400 ml beaker, 30 g of the aluminum-magnesium-hydroxy powder from Examples 12 to 15 was suspended in paraffin oil (type "Pioneer 2660," highly viscous, made by Hansen & Rosenthal, Hamburg) and was heated under stirring to 90° C. with the aid of a heating plate. Then 0.1 g polyoxyethylene-(4)-lauryl alcohol (0.5% with reference to the powder used) was added and the mixture was heated under stirring to about 120° C. until the suspension began to foam slightly. The foaming results from traces of water. Without being cooled further, the suspension was treated for about 30 seconds with high shear forces (IKA-Laboratory "Turrax") until it thickened. Then the suspension was cooled under vacuum in a desiccator and with slight stirring.

The results were transparent gels of different viscosity and stability.

TABLE 6

Production of Mineral Oil Gels Containing Al-Mg-Hydroxy Stearates of Different Compositions

| Example No. | Al-Mg-Hydroxy Stearate fr. Example | Atom Ratio Al | Mg | Yield g | % |
|---|---|---|---|---|---|
| 25 | 2 | 3 | 13 | 198 | 99 |
| 26 | 3 | 5 | 10 | 197 | 98 |
| 27 | 4 | 7 | 7 | 195 | 97 |
| 28 | 5 | 9 | 4 | 198 | 99 |

EXAMPLES 29 TO 32

Production of mineral oil gels including different powder concentrations

In a 400 ml beaker, aluminum-magnesium-hydroxy stearate powder from Example 16 was suspended in paraffin oil (type "Pioneer 2660", highly viscous, made by Hansen & Rosenthal, Hamburg) and was heated under stirring to 90° C. with the aid of a heating plate. Then 0.1 g polyoxyethylene-(4)-lauryl alcohol (0.5% with reference to the powder used) was added and the mixture was heated under stirring to about 120° C. until the suspension began to foam slightly. The foaming resulted from traces of water. Without being cooled further, the suspension was treated for about 30 seconds with high shear forces (using, for example, a IKA-Laboratory "Turrax") until it thickened. Then the suspension was cooled under vacuum in a desiccator and with slight stirring.

The result in each case was a colorless, transparent gel of different viscosity.

TABLE 7
Production of Mineral Oil Gels Having Different Powder Concentrations

| Example No. | Paraffin Oil (g) | Al-Mg-Hydroxy Stearate (g) | Al-Mg-Hydroxy Stearate (%) | Yield (g) | Yield (%) |
| --- | --- | --- | --- | --- | --- |
| 29 | 190 | 10 | 5 | 198 | 99 |
| 30 | 180 | 20 | 10 | 199 | 100 |
| 31 | 174 | 26 | 13 | 200 | 100 |
| 32 | 160 | 40 | 20 | 199 | 99 |

EXAMPLES 33 TO 40

Production of gels containing different liquids

In a 400 ml beaker, 30 g of the aluminum-magnesium-hydroxy palmitate powder from Example 17 was suspended in an organic liquid and heated under stirring to 90° C. with the aid of a heating plate. Then 0.1 g polyoxyethylene-(4)-lauryl alcohol (0.5% with reference to the powder used) was added and the mixture was heated further under stirring to about 120° C. until the suspension began to foam slightly. The foaming was the result of traces of water. Without being cooled further, the suspension was treated for about 30 seconds with high shear forces (IKA-Laboratory "Turrax") until it thickened. Then the suspension was cooled under vacuum in a desiccator with slight stirring.

TABLE 8
Production of Gels Containing Different Organic Liquids

| Example No. | Organic Liquid | Yield g | Yield % |
| --- | --- | --- | --- |
| 33 | isopropyl myristate (1) | 190 | 95 |
| 34 | cyclomethicone (pentamer) (2) | 194 | 97 |
| 35 | cyclomethicone (tetramer) (2) | 192 | 96 |
| 36 | castor oil (3) | 190 | 95 |
| 37 | jojoba oil (4) | 190 | 95 |
| 38 | 2-octyl-dodecanol (1) | 170 | 85 |
| 39 | di-octyl adipate (1) | 190 | 95 |
| 40 | lanolin (4) | 185 | 92 |

EXAMPLE 41

Production of gel including mineral oil

In a laboratory mixer (type "Unimix" made by Hagen & Rinau, Bremen) holding a maximum of 5 kg, 400 g powder from Example 17 was suspended at room temperature in 3600 g paraffin oil (type "Pioneer 2660", highly viscous, made by Hansen & Rosenthal, Hamburg), then 0.5% polyoxyethylene-(4)-lauryl alcohol was added and the mixture was heated with gentle stirring to 120° C. The heating device was turned off and the suspension was treated for 10 minutes with high shear forces (using a "Turrax" stirrer). This caused the temperature to increase to about 130° C., which was maintained for about 20 minutes. Then the suspension was cooled to room temperature in a vacuum (about 0.6 bar) within two hours.

The yield of colorless, transparent gel was quantitative.

Physical Characteristics

The experiments in Examples 25 to 28 show that gels are obtained even with changing Al:Mg ratios, but that they may exhibit instabilities if the ratio deviates from 5:10.

TABLE 9
Comparison of the Gels With Mineral Oil Produced From Different Al-Mg-Hydroxy Stearate Compositions

| Gel from Example | Appearance | Micropenetration 0.1 mm | −18° C. 1 day after thawing | 3 months at room temperature | 1 week at 50° C. |
| --- | --- | --- | --- | --- | --- |
| 25 | colorless/transparent | 70 | A | B | B |
| 26 | colorless/transparent | 108 | A | A | A |
| 27 | white | 550 | A | D | D |
| 28 | white | 209 | A | C | C |

Stability evaluation:
A = stable
B = slight inhomogeneity
C = beginning to separate
D = noticeable separation The table below gives an overview of the increase (measured by way of micropenetration at 25° C.) of the stability of the gels from Examples 29 to 32 including different powder percentages. Stability increased with increasing powder content.

TABLE 10
Comparison of Gels Having Different Powder Concentrations

| Gel from Example | Powder concentration | Micropenetration 0.1 mm | −18° C. 1 day after thawing | 3 months at room temperature | 1 week at 50° C. |
| --- | --- | --- | --- | --- | --- |
| 29 | 5 | 330 | A | A | B |
| 30 | 10 | 124 | A | A | A |
| 31 | 13 | 65 | A | A | A |
| 32 | 20 | 42 | A | A | A |

Stability evaluation:
A = stable
B = slightly inhomogeneous
C = beginning to separate
D = noticeable separation To obtain an illustrative comparison of the consistency, the micropenetration of Vaseline was determined to be 103 (0.1 mm). The lower the value, the higher is the viscosity of the material. This comparison shows that the gels from the examples of the present application have a consistency which is comparable to "Vaseline" petroleum jelly. In the following Tables, IPM stands for isopropyl myristate; cyclomethicone tetramer and pentamer correspond to $C_8H_{24}O_4Si_4$ (octamethylcyclotetrasiloxane) and $C_{10}H_{30}O_5Si_5$ (decamethylcyclopentasiloxane), respectively; and "Miglyol" gel is a commercially available gel which comes in two different grades.

TABLE 11
Comparison of the Gels From the Examples With Vaseline With Respect to Consistency, Measured by Means of the Micropenetration Method at 25° C.

| Gel of | Type Containing | Penetration Depth (0.1 mm) |
| --- | --- | --- |
| Example 18 | mineral oil | 104 |
| Example 26 | mineral oil | 55 |
| Example 33 | IPM | 57 |
| Example 34 | cyclomethicone pentamer | 113 |
| Example 35 | cyclomethicone tetramer | 66 |
| Example 36 | castor oil | 64 |
| Example 37 | jojoba oil | 75 |
| Example 38 | 2-octyl dodecanol | 71 |
| Example 39 | di-octyl adipate | 269 |
| Example 40 | lanolin | 34 |
| "Vaseline" petroleum jelly | | 103 |

An important feature of gels used for cosmetics is their color. For the production of an absolutely white cream, for instance for a sun protection agent, white or colorless gels are advantageous. Table 12 below shows a color comparison with commerically available gels. Here the gels of the present invention unequivocally demonstrate their superiority.

TABLE 12

Comparison of the Gels From the Examples With Commercially Available Gels With Respect to Color

| Gel from | Type Containing | Color |
|---|---|---|
| Example 18 | mineral oil | colorless, transparent |
| Example 26 | mineral oil | colorless, transparent |
| bentonite gel | mineral oil | brown, transparent |
| "Miglyol gel" | neutral oil | 2 qualities, green and beige, not transparent |
| Example 33 | IPM | white, not transparent |
| bentonite gel | IPM | dark beige, not transp. |
| Example 34 | cyclomethicone pent. | white, not transparent |
| bentonite gel | cyclomethicone pent. | beige, not transparent |
| Example 35 | cyclomethicone tetr. | white, not transparent |
| bentonite gel | cyclomethicone tetr. | beige, not transparent |
| Example 36 | castor oil | light yellow, slightly transparent |
| bentonite gel | castor oil | dark brown, slightly transparent |
| Example 37 | jojoba oil | light yellow, transp. |
| Example 38 | 2-octyl dodecanol | colorless to white |
| Example 39 | di-octyl adipate | beige |
| Example 40 | lanolin | yellow |

When formulating perfumed cosmetics, it is generally disadvantageous if the non-perfume products used in the formulation have a strong odor. Table 13 below demonstrates the results of a comparison of the odor of the compounds of the present invention with commercially available products. The superiority of the gels disclosed by the present invention is again very evident.

TABLE 13

Comparison of the Gels From the Examples With Commercially Available Gels With Respect to Odor

| Gel of | Type Containing | Odor |
|---|---|---|
| Example 18 | mineral oil | no odor |
| Example 26 | mineral oil | no odor |
| bentonite gel | mineral oil | propylene carbonate odor |
| "Miglyol" gel | neutral oil | green color, unique odor |
| "Miglyol" gel | neutral oil | beige color, no odor |
| Example 33 | IPM | no odor |
| bentonite gel | IPM | no odor |
| Example 34 | cyclomethicone pent. | no odor |
| bentonite gel | cyclomethicone pent. | strong ethanol odor |
| Example 35 | cyclomethicone tetr. | no odor |
| bentonite gel | cyclomethicone tetr. | strong ethanol odor |
| Example 36 | castor oil | castor oil odor |
| bentonite gel | castor oil | castor oil odor |
| Example 37 | jojoba oil | slight jojoba oil odor |
| Example 38 | 2-octyl dodecanol | slight unique odor |
| Example 39 | di-octyl adipate | slight unique odor |
| Example 40 | lanolin | lanolin odor |

A comparison of the stabilities indicates that the gels disclosed in the present invention are more stable than the commerically available gels.

TABLE 14

Comparison of the Gels From the Examples With Commercially Available Gels With Respect to Stability

| Gel | Type containing | −18° C. 24 h aft. thaw. | Room temp. 3 mos. | 50° C. 7 days |
|---|---|---|---|---|
| Example 18 | mineral oil | A | A | A |
| Example 26 | mineral oil | A | A | A |
| bentonite gel | mineral oil | A | B | A |
| "Miglyol" gel | neutral oil | A | D | C |
| green "Miglyol" gel | neutral oil | A | B | B |
| beige Example 33 | IPM | B | A | A |
| bentonite gel | IPM | B | A | A |
| Example 34 | cyclomethicone pent. | A | A | C |
| bentonite gel | cyclomethicone pent. | A | F | C |
| Example 35 | cyclomethicone tetr. | A | A | A |
| bentonite gel | cyclomethicone tetr. | A | F | A |
| Example 36 | castor oil | A | A | A |
| bentonite gel | castor oil | A | A | A |
| Example 37 | jojoba oil | A | A | A |
| Example 38 | 2-octyl dodecanol | A | A | B |
| Example 39 | di-octyl adipate | C | B | D |
| Example 40 | lanolin | A | A | A |

Evaluation:
A = stable
B = slight inhomogeneity
C = beginning to separate
D = noticeable separation
E = total separation
F = evaporation of alcohol An important characteristic of swellable bentonites is their distinctly thixotropic and thickening behavior.

Table 15 below demonstrates viscosity as a function of shear velocity in dependence on the temperature of the gel of Example 41, measured with a "Rheomat 115" viscometer made by Contraves, Stuttgart (Measuring body DIN 125).

TABLE 15

Viscosity as a Function of Shear Velocity in Dependence on Temperature

| Shear rate* (Revolutions per Second) | Viscosity (mpa · s) of gel from Example 41 at T (°C.) | | | | |
|---|---|---|---|---|---|
| | 20° C. | 30° C. | 40° C. | 50° C. | 60° C. |
| 6.65 | 17,158 | 10,811 | 7,207 | 4,462 | 3,089 |
| 3.51 | 12,120 | 7,680 | 5,040 | 3,120 | 2,280 |
| 12.61 | 8,631 | 5,447 | 3,687 | 2,263 | 1,676 |
| 10.48 | 6,387 | 3,985 | 2,637 | 1,641 | 1,231 |
| 27.9 | 4,826 | 2,863 | 1,881 | 1,186 | 941 |
| 39.9 | 3,775 | 2,145 | 1,401 | 887 | 686 |
| 57.2 | 2,993 | 1,616 | 1,037 | 658 | 519 |
| 81.8 | 2,441 | 1,270 | 809 | 502 | 405 |
| 117.1 | 2,016 | 1,013 | 643 | 409 | 321 |
| 167.6 | 1,682 | 831 | 518 | 327 | 259 |
| 240 | 1,420 | 689 | 428 | 276 | 214 |
| 343 | 1,209 | 596 | 366 | 233 | 180 |
| 492 | 1,030 | 524 | 318 | 202 | 153 |
| 704 | 878 | 465 | 277 | 177 | 132 |
| 1008 | 758 | 421 | 252 | 162 | 120 |

*The shear rate was changed in 15 steps, each time after 30 seconds.

Table 15 very clearly demonstrates the decrease in viscosity with increase of shear velocity and temperature.

Table 16 below shows the viscosity as a function of the increase and subsequent decrease of shear velocity for the gel of Example 26 at different temperatures. Table 16 clearly shows the thixotropic behavior of the gel by the different viscosity values at the beginning and end.

TABLE 16

Viscosity as a Function of Shear Velocity in Dependence on Temperature

| Shear rate* (Revolutions per Second) | Viscosity (mpa · s) at T (°C.) | | | |
|---|---|---|---|---|
| | 20° C. | | 80° C. | |
| | Ascending | Descending | Ascending | Descending |
| 6.65 | 25,528 | 14,414 | 9,953 | 6,349 |
| 9.51 | 18,600 | 10,080 | 6,840 | 4,680 |
| 13.61 | 13,408 | 8,212 | 4,777 | 3,268 |
| 19.48 | 9,786 | 6,211 | 3,340 | 2,403 |
| 27.9 | 7,198 | 4,785 | 2,372 | 1,759 |
| 39.9 | 5,320 | 3,804 | 1,687 | 1,287 |
| 57.2 | 4,070 | 3,092 | 1,177 | 938 |
| 81.8 | 3,139 | 2,595 | 865 | 712 |
| 117.1 | 2,503 | 2,153 | 633 | 536 |
| 167.6 | 2,016 | 1,798 | 470 | 409 |
| 240 | 1,672 | 1,501 | 347 | 312 |
| 343 | 1,399 | 1,299 | 273 | 250 |
| 492 | 1,199 | 1,200 | 209 | 200 |
| 704 | 1,034 | 956 | 169 | 164 |
| 1,008 | 872 | 872 | 137 | 137 |

*The shear velocity was changed in 15 steps, each time after two minutes, ascending and descending.

As stated above, the thixotropic characteristics of gels are extremely important for cosmetics. A comparison with commercially available gels is given in Table 17 below. Viscosity was measured as a function of the increase and decrease of shear velocity at 20.C for the gel of Example 31 and bentonite gel containing mineral oil.

TABLE 17

Viscosity as a Function of Increase and Decrease of Shear Velocity at 20° C.

| Shear Velocity* (Revolutions per Second) | Gel from Example 31 Viscosity (mpa · s) | | Bentonite Gel Viscosity (mpa · s) | |
|---|---|---|---|---|
| 6.65 | 20,935 | 12,184 | 123,895 | 115,315 |
| 9.51 | 14,640 | 8,760 | 87,480 | 84,600 |
| 13.61 | 10,391 | 6,453 | 62,431 | 62,012 |
| 19.48 | 7,500 | 4,964 | 45,884 | 45,532 |
| 27.9 | 5,440 | 3,681 | 33,333 | 33,374 |
| 39.9 | 4,061 | 2,860 | 24,367 | 24,567 |
| 57.2 | 3,092 | 2,274 | 17,835 | 17,995 |
| 81.8 | 2,427 | 1,841 | 13,085 | 13,141 |
| 117.1 | 1,968 | 1,519 | 9,545 | 9,516 |
| 167.6 | 1,614 | 1,280 | 6,946 | 6,871 |
| 240 | 1,340 | 1,026 | 5,016 | 4,950 |
| 343 | 1,132 | 952 | 3,663 | 3,730 |
| 492 | 958 | 840 | 2,768 | 2,598 |
| 704 | 807 | 747 | 1,921 | 1,887 |
| 1,008 | 687 | 687 | 1,407 | 1,407 |

*The shear velocity was changed in 15 steps, each time after two minutes, ascending and descending.

A comparison of the two gels shows that the gel according to the present invention has a higher thixotropic behavior which is characterized by the greater difference between the beginning and end values.

Use of the Gel Composition in Cosmetic Compositions

To demonstrate the advantages in the use of the gels disclosed by the present invention compared to conventional gels, several finished formulations were produced and tested.

1. Production of Thermostable W/O (water-in-oil) sun creams

One problem that has not been completely solved in the manufacture of sun creams is the instability of the viscosity of creams at higher temperatures up to 60° C., as may occur in the sun at the beach or in display windows. At these temperatures, a conventional cream becomes watery and can no longer be easily applied. If the gel produced in Example 18 is incorporated up to 15% in a cream, its viscosity at 60° C. is still high enough that the cream can be applied well. Additionally, the long-term stability of the cream is greatly improved.

The creams listed below were tested for comparison:

TABLE 18

| Formulation (in %) | | A | B | C | D | E | F |
|---|---|---|---|---|---|---|---|
| gel of Example 18 | | 15 | — | — | — | — | — |
| bentonite gel with mineral oil | (1) | — | 15 | — | — | — | — |
| "Miglyol" gel | (2) | — | — | 15 | — | — | — |
| aluminum stearate | (3) | — | — | — | 2.3 | — | — |
| magnesium stearate | (3) | — | — | — | — | — | 2.3 |
| paraffin oil | (4) | 8.5 | 8.5 | 8.5 | 21.2 | 23.5 | 21.2 |
| cetyl alcohol | (5) | 2 | 2 | 2 | 2 | 2 | 2 |
| sorbitane monoisostearate | (6) | 3 | 3 | 3 | 3 | 3 | 3 |
| lanolin | (7) | 1 | 1 | 1 | 1 | 1 | 1 |
| microwax ("HP 67") | (8) | 6 | 6 | 6 | 6 | 6 | 6 |
| water | | 63.8 | 63.8 | 63.8 | 63.8 | 63.8 | 63.8 |
| "Phenonip" (preservative) | (9) | 0.2 | 0.2 | 0.2 | 0.2 | 0.2 | 0.2 |
| perfume oil | | 0.5 | 0.5 | 0.5 | 0.5 | 0.5 | 0.5 |

These products were manufactured by the following:
(1) NL Chemicals, Belgium
(2) Dynamit Nobel, Troisdorf, FRG
(3) Bärlocher, Munich, FRG
(4) Hansen & Rosenthal, Bremen, FRG
(6) Henkel, Düsseldorf, FRG
(7) Nordmann & Rassmann, Hamburg, FRG
(8) Schütz, Oberursel, FRG
(9) Damm Hamburg, FRG The cream was produced by melting the oil phase at 80° C. and adding water at 80° C. while stirring. Stirring continued for about 5 minutes and the mixture was then cooled to about 35° C. Then perfume oil and a preservative were added.

Figure 3:
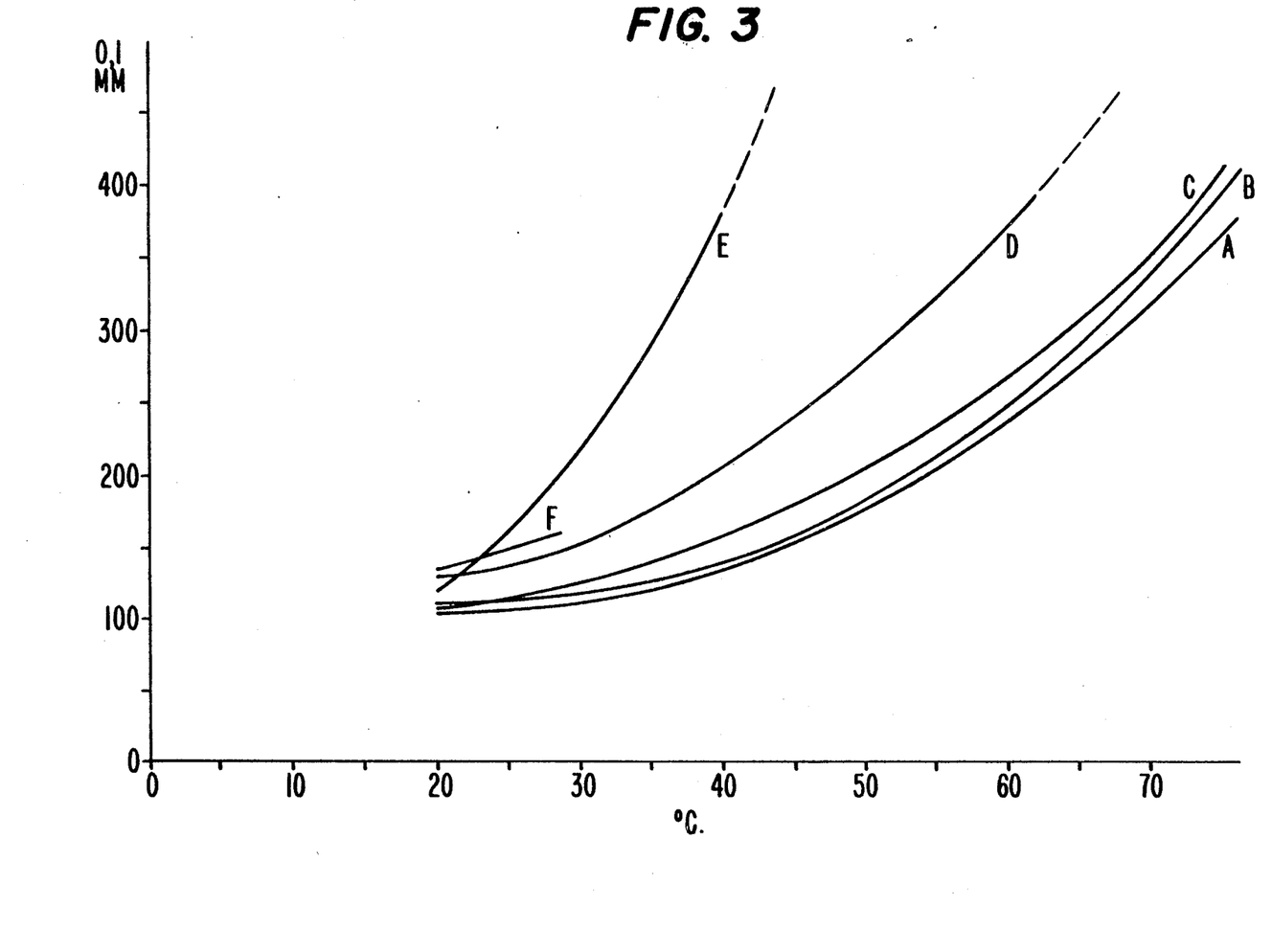
FIG. 3 is a graph comparing the thermal stability of the viscosities of formulations A-F.

The consistency of the creams was again determined by way of micropenetration. The attached FIG. 3 shows that the creams produced in the conventional manner on a hydrocarbon base became liquid at above 40° C. (dashed line) while the formulation A including the gel of Example 18 still had a semi-firm consistency at temperatures above 70° C.

Another problem in the production of suspensions for cosmetics is the rapid sedimentation of the insoluble components. For example, in antiperspirant aerosols composed of a propellant gas, silicone oil and the insoluble active substance aluminum chlorhydrate, the active substance should remain homogeneously distributed in the suspension for a long time after the container has been shaken. Otherwise, varying concentrations would result during use depending on the length of time after shaking. The same problem also occurs in suspension roll-ons. The gels of Examples 33 to 35 are ideally suitable for such uses. For a comparison with and without rheological additive, the following aerosol formulations were prepared and tested for their settling behavior. For this purpose, the settling volume was determined after various periods of time. The aerosol gas bottle was shaken 20 times vertically and 20 times horizontally and was then left standing. The total volume of the suspension is 100%. The settling volume is the total volume minus the layer of propellant gas after the respective time periods, given in volume percentages.

TABLE 19

| Aerosol Formulations (in %) | A | B | C |
| --- | --- | --- | --- |
| gel from Example 35 | 5 | — | — |
| bentonite gel (tetramer) | — | 5 | — |
| cyclomethicone (tetramer) | 3 | 3 | 8 |
| isopropyl myristate | 2 | 2 | 2 |
| ethanol | 2 | 2 | 2 |
| aluminum chlorhydrate | 3 | 3 | 3 |
| perfume oil | 0.5 | 0.5 | 0.5 |
| butane | 84.5 | 84.5 | 84.5 |

TABLE 20

| Suspension Roll-On Formulations | D | E | F |
| --- | --- | --- | --- |
| gel from Example 34 | 10 | — | — |
| bentonite gel with cyclomethicone (pentamer) | — | 10 | — |
| cyclomethicone (pentamer) | 64.5 | 64.5 | 74.5 |
| isopropyl myristate | 2 | 2 | 2 |
| ethanol | 3 | 3 | 3 |
| aluminum chlorhydrate | 20 | 20 | 20 |
| perfume oil | 0.5 | 0.5 | 0.5 |

Production

In the sequence listed, the components gel, isopropyl myristate, ethanol, aluminum chlorhydrate, and perfume oil were homogeneously stirred into the cyclomethicone (pentamer).

Figure 4:
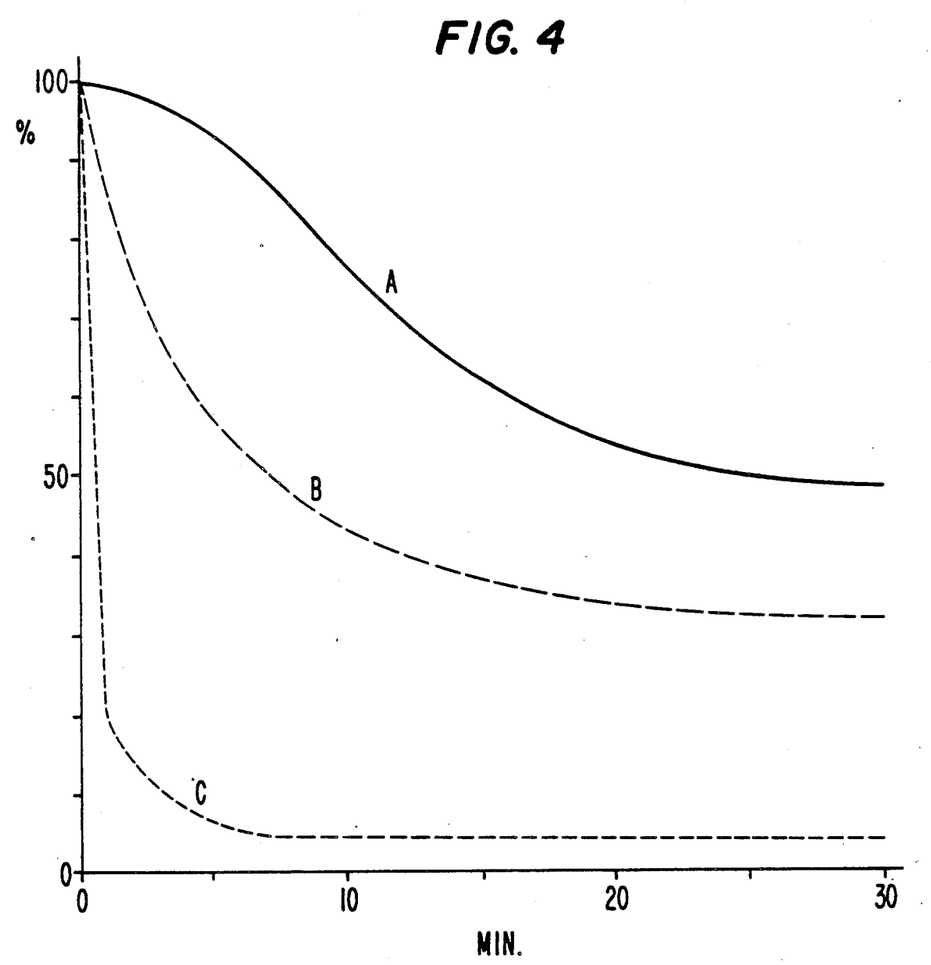
FIG. 4 is a graph showing sedimentation curves for formulations A-C in cyclomethicone tetramer.
Figure 5:
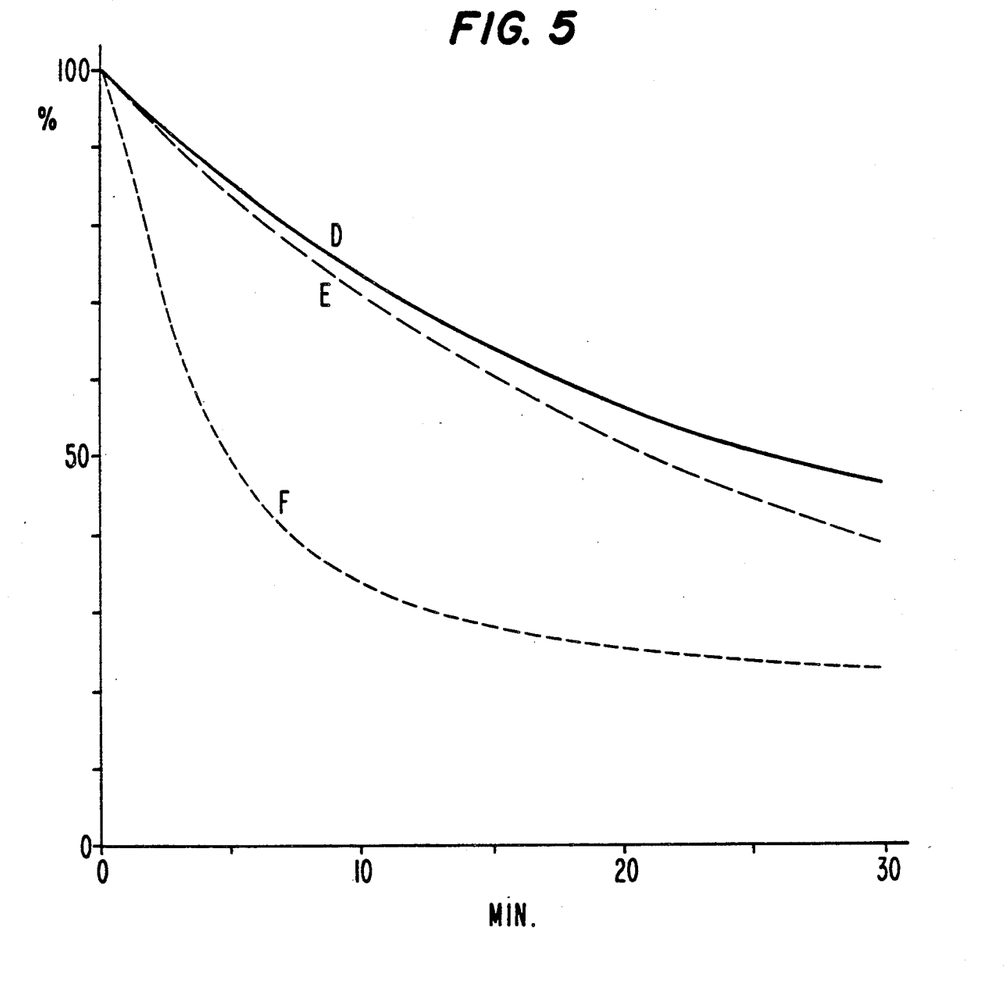
FIG. 5 shows sedimentation curves for formulations D-F in cyclomethicone pentamer.

FIGS. 4 and 5 show the settling curves for the formulations. The difference between formulations with and without rheological additive and thus the advantage of the gels disclosed in the present invention is clearly evident.

Another problem in finished cosmetics is caused, especially in lipsticks and lip gloss preparations, by changing storage temperatures, (for example, between night and day) and the sensitivity of the consistency to temperatures above 40° C., for example, during the summer. Yet another problem is that pigments settle out of the liquid phase during manufacture.

For an examination of the performance of the compositions according to the invention under conditions like those mentioned above, the formulations below were produced in the laboratory:

TABLE 21

| Formulations (in %) | | A | B | C |
| --- | --- | --- | --- | --- |
| gel of Example 33 | | — | 10 | — |
| gel of Example 36 | | — | — | 10 |
| castor oil | (1) | 51.2 | 50.2 | 41.2 |
| isopropyl myristate | (2) | 10 | 1 | 10 |
| ozocerite | (3) | 5 | 5 | 5 |
| candelilla wax | (3) | 9 | 9 | 9 |
| "Amerchol L 101" | (4) | 2.5 | 2.5 | 2.5 |
| ground pigment* | | 20 | 20 | 20 |
| BHT | (1) | 0.1 | 0.1 | 0.1 |
| propylparaben | (1) | 0.1 | 0.1 | 0.1 |
| perfume oil | | 0.5 | 0.5 | 0.5 |

*ground pigment: 80% of 1A and 20% of 1B
1A = 50% titanium dioxide in castor oil (5)
2B = 3% erythrosine lacquer (red) in castor oil (5)

These products were manufactured by the following:
(1) Merck, Darmstadt, FRG
(2) Henkel, Düsseldorf, FRG
(3) Schütz, Oberursel, FRG
(4) Nordmann & Rassmann, Hamburg, FRG
(5) BASF, Ludwigshafen, FRG Production of the lipsticks according to formulations A, B and C of Table 21:

The components (except for the ground pigment, BHT, propylparaben and perfume oil) were melted at 90° C. while stirring, where then cooled in a vacuum to about 70° C. and the ground pigment was added. Then the remaining components were added and the substance was placed into individual containers.

For an examination of changing storage temperatures, the above formulations were stored for one night at +5° C. and then for 8 hours at 40° C. A visual comparison of the samples clearly showed formulation A to release oil, while formulations B and C remained intact.

To observe possible sedimentation of pigments in the liquid phase, formulations A to C were remelted and poured at 80° C. into glass tubes having an inner diameter of 1 cm and a length of 10 cm, and were then allowed to cool at room temperature. This brought about a slight difference in color intensity between the upper and lower portions of formulation A while formulations B and C exhibited no differences.

The present disclosure relates to the subject matter disclosed in Federal Republic of Germany Patent Application No. 37 32 265.6 on Sept. 25th, 1987, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. A gel composition comprising:
an aluminum magnesium hydroxy compound of the formula $$Al_xMg_y(OH)_{35-z}R_z \cdot n\, H_2O$$

where R represents the anion of a monocarboxylic acid having 2 to 22 carbon atoms and x, y and z are defined by $$0 \leq n \leq 10$$

$$3 \leq x \leq 9$$

$$4 \leq y \leq 13$$

$$3 \leq z \leq 5$$

and $$3x + 2y = 35;$$

and an organic, lipophilic compound which is liquid at 20° C.

2. A gel composition as defined in claim 1, wherein the organic, lipophilic compound is at least one compound from selected the group consisting of
vegetable and animal fats, oils and waxes;
paraffin hydrocarbons;
silicone oils;
aliphatic and aromatic esters; and
higher alcohols and ethers.

3. A gel composition as defined in claim 1, further comprising from about 0.01% to 20% by weight with respect to the aluminum magnesium hydroxy compound, of a polar additive.

4. A gel composition as defined in claim 3, comprising from about 0.05% to 1% by weight with respect to the aluminum magnesium hydroxy compound, of the polar additive.

5. A gel composition as defined in claim 3, wherein the polar additive is selected from the group consisting of propylene carbonate, polyoxyethylene-(4)-lauryl alcohol, a mixture of water/methanol containing from 95 to 75% by weight methanol, a mixture of water/ethanol containing from 95 to 75% by weight ethanol, and a mixture of water/acetone containing from 95 to 75% by weight acetone.

6. A gel composition as defined in claim 1, wherein the concentration of the organic, lipophilic compound is 95 to 75% by weight.

7. A gel composition as defined in claim 6 wherein the concentration of the organic, lipophilic compound is 90 to 80% by weight.

8. A gel composition as defined in claim 1, wherein the amount of the aluminum magnesium hydroxy compound is about to 25% by weight with respect to the gel composition.

9. A gel composition as claimed in claim 8, wherein the amount of the aluminum magnesium hydroxy compound is 10 to 20% by weight of the gel composition.

10. A gel composition as defined in claim 1, wherein $x=5$, $y=10$ and $z=4$.

11. A gel composition as defined in claim 1, wherein said at least one monocarboxylic acid anion is a mixture of aliphatic monocarboxylic acid anions having from 16 to 18 carbon atoms.

12. A gel composition as defined in claim 1, having the formula $$Al_5Mg_{10}(OH)_{31}R_4 \cdot nH_2O$$

wherein R represents at least one monocarboxylic acid anion having from 16 to 18 carbon atoms and $0 \leq n \leq 10$.

13. A method of producing a gel composition useful as a thickening agent, comprising the steps of:
mixing an aluminum magnesium hydroxy compound having a t laminar structure of the formula $$Al_xMg_y(OH)_{35-z}R_z \cdot n H_2O$$

where R represents the anion of a monocarboxylic acid having 2 to 22 carbon atoms and n, x, y and z are defined by $$0 \leq n \leq 10$$

$$3 \leq x \leq 9$$

$$4 \leq y \leq 13$$

$$3 \leq z \leq 5$$

and $$3x + 2y = 35;$$

with an organic, lipophilic compound which is liquid at 20° C. to produce a reaction mixture; and
heating said reaction mixture to a temperature from about 120° C. to about 130° C. under the influence of shear forces.

14. A method as defined in claim 13, wherein $x=5$, $y=10$ and $z=4$.

15. A method as defined in claim 13, wherein said at least one monocarboxylic acid anion is a mixture of aliphatic monocarboxylic acid anions having from 16 to 18 carbon atoms.

16. A method as defined in claim 13, wherein the aluminum magnesium hydroxy compound has the formula $$Al_5Mg_{10}(OH)_{31}R_4 \cdot nH_2O$$

wherein R represents at least one monocarboxylic acid anion having from 16 to 18 carbon atoms and $0 \leq n \leq 10$.

17. In a cosmetic composition the improvement comprising an effective gel-forming amount of an aluminum magnesium hydroxy compound of the formula $$Al_xMg_y(OH)_{35-z}R_z \cdot n H_2O$$

where R represents the anion of a monocarboxylic acid having 2 to 22 carbon atoms and n, x, y and z are defined by $$0 \leq n \leq 10$$

$$3 \leq X \leq 9$$

$$4 \leq y \leq 13$$

$$3 \leq z \leq 5$$

and $$3x + 2y = 35;$$

and an organic, lipophilic compound which is liquid at 20° C.

18. A composition as defined in claim 17, wherein $x=5$, $y=10$ and $z=4$.

19. A composition as defined in claim 17, wherein said at least one carboxylic acid anion is a mixture of aliphatic monocarboxylic acid anions having from 16 to 18 carbon atoms.

20. A composition as defined in claim 17, wherein the aluminum magnesium hydroxy compound has the formula $$Al_5Mg_{10}(OH)_{31}R_4 \cdot nH_2O$$

wherein R represents at least one monocarboxylic acid anion having from 16 to 18 carbon atoms and $0 \leq n \leq 10$.

* * * * *

UNITED STATES PATENT AND TRADEMARK OFFICE
CERTIFICATE OF CORRECTION

PATENT NO. : 5,073,573
DATED     : December 17, 1991
INVENTOR(S) : Roland Martin et al.

It is certified that error appears in the above-identified patent and that said Letters Patent is hereby corrected as shown below:

Please correct the title page to read as follows:

Line 2, Roland Martin et al.

Under [75] please correct the first inventor's city of residence to read as follows:

Inventors: Roland Martin, Weinheim

Signed and Sealed this

Thirteenth Day of April, 1993

*Attest:*

STEPHEN G. KUNIN

*Attesting Officer*     *Acting Commissioner of Patents and Trademarks*